United States Patent
Acosta-Acevedo

(10) Patent No.: US 9,700,399 B2
(45) Date of Patent: Jul. 11, 2017

(54) STOPPER TO PREVENT GRAFT MATERIAL SLIPPAGE IN A CLOSED WEB STENT-GRAFT

(75) Inventor: Luz Acosta-Acevedo, Rohnert Park, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 807 days.

(21) Appl. No.: 13/457,475

(22) Filed: Apr. 26, 2012

(65) Prior Publication Data

US 2013/0289700 A1 Oct. 31, 2013

(51) Int. Cl.
*A61F 2/06* (2013.01)
*A61F 2/07* (2013.01)
(Continued)

(52) U.S. Cl.
CPC .............. *A61F 2/07* (2013.01); *A61F 2/2418* (2013.01); *A61F 2/86* (2013.01); *A61F 2/89* (2013.01); *A61F 2/90* (2013.01); *A61F 2002/072* (2013.01); *A61F 2002/075* (2013.01)

(58) Field of Classification Search
CPC ...... A61F 2/02; A61F 2/04; A61F 2/06; A61F 2/07; A61F 2/82; A61F 2/86; A61F 2/88; A61F 2/89; A61F 2/90; A61F 2/95; A61F 2/954; A61F 2/958; A61F 2002/041; A61F 2002/043; A61F 2002/044; A61F 2002/045; A61F 2002/046; A61F 2002/047; A61F 2002/048; A61F 2002/061; A61F 2002/072; A61F 2002/075; A61F 2002/077; A61F 2002/821; A61F 2002/823;
(Continued)

(56) References Cited

U.S. PATENT DOCUMENTS

| 6,051,020 A | 4/2000 | Goicoechea et al. |
| 6,517,570 B1 | 2/2003 | Lau et al. |

(Continued)

FOREIGN PATENT DOCUMENTS

| CN | 1961845 | 5/2007 |
| CN | 102100587 | 6/2011 |

(Continued)

OTHER PUBLICATIONS

Oxford Dictionaries, Abut, 2016, www.oxforddictionaries.com.*

(Continued)

*Primary Examiner* — Jonathan Miles
*Assistant Examiner* — Kendra Obu

(57) ABSTRACT

A stent-graft has a closed web configuration in which end stent crowns or apexes do not extend beyond an end of a tubular graft. In order to permit interaction of the endmost crowns with tip capture fingers or prongs of a delivery system, the graft covers the endmost crowns but the endmost crowns are not coupled to the graft material and thus free to interact with the delivery system. In order to prevent slippage of the graft material at the endmost crowns and secure the longitudinal position of the graft material, one of a pair of stoppers is coupled on each of the opposing struts between which the unattached endmost crown is formed. In an embodiment, the stoppers are cylindrical tubes of a radiopaque material having a longitudinally-extending slit in a wall thereof.

20 Claims, 4 Drawing Sheets

(51) Int. Cl.
*A61F 2/90* (2013.01)
*A61F 2/86* (2013.01)
*A61F 2/24* (2006.01)
*A61F 2/89* (2013.01)

(58) Field of Classification Search
CPC .......... A61F 2002/825; A61F 2002/826; A61F 2002/828; A61F 2002/8483; A61F 2002/8486; A61F 2002/91591; A61F 2002/91508; A61F 2002/91516; A61F 2002/91525; A61F 2002/91533; A61F 2002/91541; A61F 2002/91558; A61F 2002/91556; A61F 2002/91566; A61F 2002/91575; A61F 2002/9505; A61F 2002/9511; A61F 2002/9517; A61F 2002/9522; A61F 2002/9528; A61F 2002/9534; A61F 2002/9583; A61F 2002/9586; A61F 2002/9665; A61F 2/24; A61F 2/2415; A61F 2/2409; A61F 2/2412; A61F 2/2418; A61F 2/2442; A61F 2/2445; A61F 2/2454; A61F 2/2451; A61F 2/2463; A61F 2/2475; A61F 2/2478
See application file for complete search history.

(56) References Cited

U.S. PATENT DOCUMENTS

| | | | |
|---|---|---|---|
| 7,226,474 B2* | 6/2007 | Iancea et al. | 623/1.13 |
| 7,238,198 B2 | 7/2007 | Hartley et al. | |
| 7,399,314 B2 | 7/2008 | Butaric et al. | |
| 2003/0199973 A1 | 10/2003 | Chuter et al. | |
| 2004/0054396 A1* | 3/2004 | Hartley | A61F 2/07 623/1.13 |
| 2004/0167619 A1* | 8/2004 | Case et al. | 623/1.34 |
| 2007/0244541 A1 | 10/2007 | Schulman | |
| 2007/0270942 A1 | 11/2007 | Thomas | |
| 2009/0299462 A1* | 12/2009 | Fawzi et al. | 623/1.13 |
| 2010/0114296 A1* | 5/2010 | Case et al. | 623/1.16 |
| 2011/0040369 A1 | 2/2011 | Rasmussen et al. | |
| 2011/0071614 A1 | 3/2011 | Majercak et al. | |
| 2013/0116773 A1* | 5/2013 | Roeder et al. | 623/1.15 |

FOREIGN PATENT DOCUMENTS

| | | |
|---|---|---|
| EP | 1075825 | 2/2001 |
| EP | 1847235 | 10/2007 |
| JP | 2011/67630 | 4/2011 |
| WO | WO2009/124124 | 10/2009 |
| WO | 2010101070 A1 | 2/2010 |
| WO | WO2012/117683 | 9/2012 |

OTHER PUBLICATIONS

Appln No. 201380022001.X, The State Intellectual Property Office of The People's Republic of China, First Office Action, mailed Oct. 9, 2015, 14pgs.

Appln No. JP2015-508946, Japanese 1$^{st}$ Office Action, mailed Dec. 19, 2016, 5pgs.

* cited by examiner

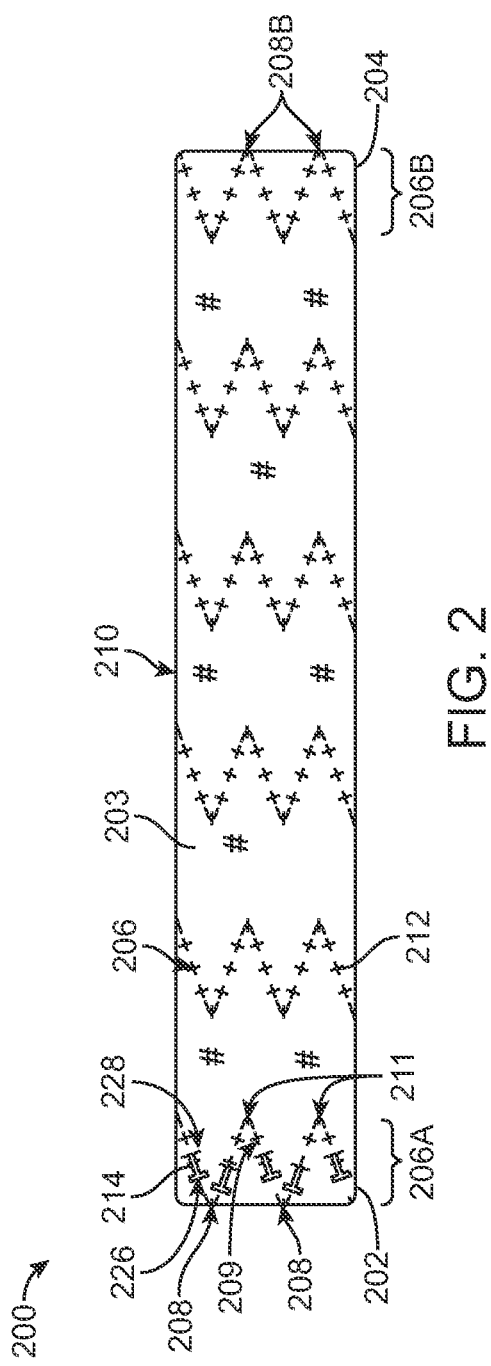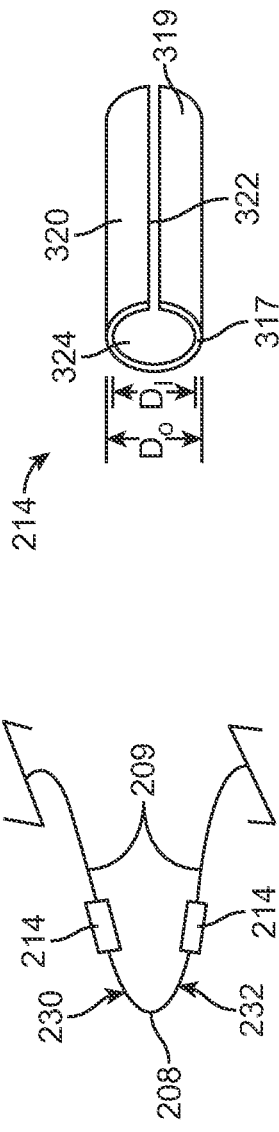

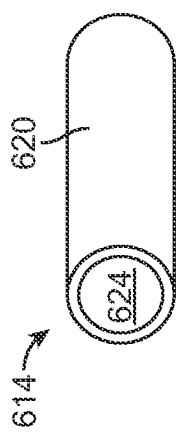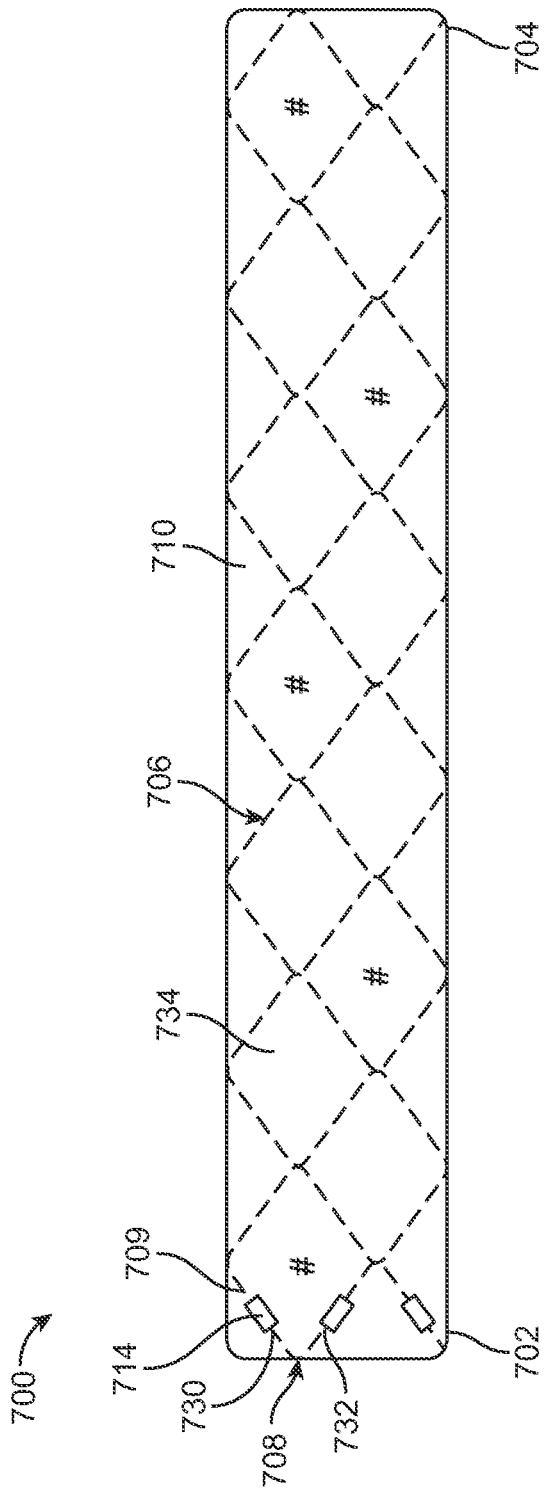
FIG. 6
FIG. 7

STOPPER TO PREVENT GRAFT MATERIAL SLIPPAGE IN A CLOSED WEB STENT-GRAFT

BACKGROUND

Field of the Invention

The invention is related in general to implantable prostheses and in particular to stent-grafts.

Related Art

Prostheses for implantation in blood vessels or other similar organs of the living body are, in general, well known in the medical art. For example, prosthetic vascular grafts constructed of biocompatible materials have been employed to replace or bypass damaged or occluded natural blood vessels. In general, endovascular grafts typically include a graft anchoring component that operates to hold a tubular graft component of a suitable graft material in its intended position within the blood vessel. Most commonly, the graft anchoring component is one or more radially compressible stents that are radially expanded in situ to anchor the tubular graft component to the wall of a blood vessel or anatomical conduit. Thus, endovascular grafts are typically held in place by mechanical engagement and friction due to the opposition forces provided by the radially expandable stents.

Grafting procedures are also known for treating aneurysms. Aneurysms result from weak, thinned blood vessel walls that "balloon" or expand due to aging, disease and/or blood pressure in the vessel. Consequently, aneurysmal vessels have a potential to rupture, causing internal bleeding and potentially life threatening conditions. Grafts are often used to isolate aneurysms or other blood vessel abnormalities from normal blood pressure, reducing pressure on the weakened vessel wall and reducing the chance of vessel rupture. As such, a tubular endovascular graft may be placed within the aneurysmal blood vessel to create a new flow path and an artificial flow conduit through the aneurysm, thereby reducing if not nearly eliminating the exertion of blood pressure on the aneurysm.

In general, rather than performing an open surgical procedure to implant a bypass graft that may be traumatic and invasive, endovascular grafts which may be referred to as stent-grafts are preferably deployed through a less invasive intraluminal delivery procedure. More particularly, a lumen or vasculature is accessed percutaneously at a convenient and less traumatic entry point, and the stent-graft is routed through the vasculature to the site where the prosthesis is to be deployed. Intraluminal deployment is typically effected using a delivery catheter with coaxial inner and outer tubes arranged for relative axial movement. For example, a self-expanding stent-graft may be compressed and disposed within the distal end of an outer catheter tube distal of a stop fixed to the inner member. The catheter is then maneuvered, typically routed through a body lumen until the end of the catheter and the stent-graft is positioned at the intended treatment site. The stop on the inner member is then held stationary while the outer tube of the delivery catheter is withdrawn. The inner member prevents the stent-graft from being withdrawn with the sheath. As the sheath is withdrawn, the stent-graft is released from the confines of the sheath and radially self-expands so that at least a portion of it contacts and substantially conforms to a portion of the surrounding interior of the lumen, e.g., the blood vessel wall or anatomical conduit.

In recent years to improve alignment during deployment of a stent-graft having self-expanding stents, various tip capture mechanisms have been incorporated into the delivery system used for percutaneously delivering the prosthesis. For example, U.S. Patent Application Publication No. 2006/0276872 to Arbefuielle et al. and U.S. Patent Application Publication No. 2009/0276207 to Glynn et al., both herein incorporated by reference in their entirety, describe tip capture mechanisms that restrain the proximal end stent of the stent-graft while the remainder of the stent-graft expands, then releases the proximal end stent. The proximal end stent is attached to the graft material of the stent-graft so as to have an "open web" or "free flow" proximal end configuration in which the endmost crowns thereof extend past or beyond the graft material such that the endmost crowns are exposed or bare, and thus free to interact with a tip capture mechanism and couple the prosthesis to the delivery system. The open web proximal end configuration allows blood flow through the endmost crowns for perfusion during and/or after implantation. FIGS. 1A and 1B illustrate a delivery system 10 having a tip capture mechanism 12 designed to couple or interact with a stent-graft 14 having an open web or free flow proximal end configuration 16. More particularly, endmost crowns 18 engage or hook around retractable finger or prong-like elements 20 of the tip capture mechanism. When an outer delivery shaft 22 is retracted to allow stent-graft 14 to self-expand, endmost crowns 18 of the end stent 15 remain hooked around tip capture fingers 20, as shown in FIG. 1A. To release end stent 15, a shaft 24 coupled to finger or prong-like elements 20 is retracted and end stent 15 is allowed to self-expand, as shown in FIG. 1B. The Captivia Delivery System manufactured by Medtronic Vascular, Inc. of Santa Rosa, Calif. is one example of a delivery system having a tip capture mechanism as described above, which may be used for delivering endovascular stent-grafts such as the Valiant Thoracic Stent-graft manufactured by Medtronic Vascular, Inc. of Santa Rosa, Calif.

Tip capture mechanisms have improved accuracy of deployment of self-expanding stent-grafts having open web or free flow configurations. However, in some cases a closed web configuration may be required or chosen due to application and/or user preferences. In a closed web configuration, the endmost crowns do not extend past or beyond the graft material but rather are covered by graft material. Embodiments hereof relate to a stent-graft having a closed web configuration that may interact with a tip capture mechanism of a delivery system.

SUMMARY

Embodiments hereof relate to a prosthesis for implantation within a body lumen. The prosthesis includes a tubular graft of a graft material and a stent comprised of a plurality of crowns and a plurality of struts with each crown being formed between a pair of opposing struts. The stent is coupled to the graft material proximate to an end of the tubular graft so as to have a first set of crowns adjacent to the end of the tubular graft and a second set of crowns distant from the end of the tubular graft relative to the first set of crowns. A pair of stoppers is coupled adjacent to each crown of the first set of crowns, wherein each stopper has a tubular configuration and is attached to a respective one of the pair of opposing struts that the crown is formed between. At least one stitch is made adjacent to each end of each stopper. The stitches secure a longitudinal position of the graft material relative to each stopper and the strut it is attached to such that the first set of crowns are covered by and free of direct attachment to the graft material of the tubular graft.

Embodiments hereof also relate to a prosthesis that includes a tubular graft of a graft material and a stent coupled to the tubular graft and having endmost crowns that are inwardly spaced from an end of the tubular graft. Each endmost crown is a curved segment formed between a pair of opposing struts. One or more of the endmost crowns are covered by and free of direct attachment to the graft material of the tubular graft. A pair of stoppers is coupled adjacent to each endmost crown that is covered by and free of direct attachment to the graft material, wherein each stopper has a tubular configuration and is attached to a respective one of the pair of opposing struts that the crown is formed between. At least one stitch is made adjacent to each end of each stopper, wherein the stitches abut against the ends of each stopper.

Embodiments hereof also relate to a prosthesis that includes a tubular graft of a graft material and a stent coupled to the tubular graft and including a plurality of crowns and a plurality of struts with each crown being formed between a pair of opposing struts. The stent has endmost crowns that are proximate to an end of the tubular graft, and one or more of the endmost crowns are covered by and free of direct attachment to the graft material of the tubular graft. A pair of stoppers is coupled adjacent to each endmost crown that is covered by and free of direct attachment to the graft material. Each stopper is attached to a respective one of the pair of opposing struts that the crown is formed between. An outer diameter of each stopper is greater than an outer diameter of the stent struts such that each stopper end creates a raised feature relative to the stent strut. At least one stitch is made adjacent to each end of each stopper, wherein the stitches abut against the respective raised feature created by each stopper.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 2 is a side view of a stent-graft having a closed web configuration which is configured to permit interaction with tip capture fingers of a delivery system, wherein endmost crowns of an end stent are not coupled to the graft material and include stoppers to prevent slippage of the graft material according to an embodiment hereof.

FIG. 2A is an enlarged view of an endmost crown of FIG. 2, wherein the endmost crown is shown with stoppers but removed from the graft material for clarity purposes.

FIG. 3 is a perspective view of a stopper of FIG. 2, removed from the stent-graft for illustrative purposes, wherein the stopper is a slit tube.

FIG. 4 and FIG. 5 are enlarged illustrations of an end stent crown of FIG. 2 having a pair of stoppers coupled to the stent, wherein FIG. 4 illustrates the inside surface of the graft material and FIG. 5 illustrates the outside surface of the graft material.

FIG. 6 is a perspective view of a stopper according to another embodiment hereof, wherein the stopper is a tube.

FIG. 7 is a side view of a stent-graft having a stent configuration according to another embodiment hereof, wherein endmost crowns of the stent are not coupled to the graft material and include stoppers to prevent slippage of the graft material.

DETAILED DESCRIPTION

Figure 1A:
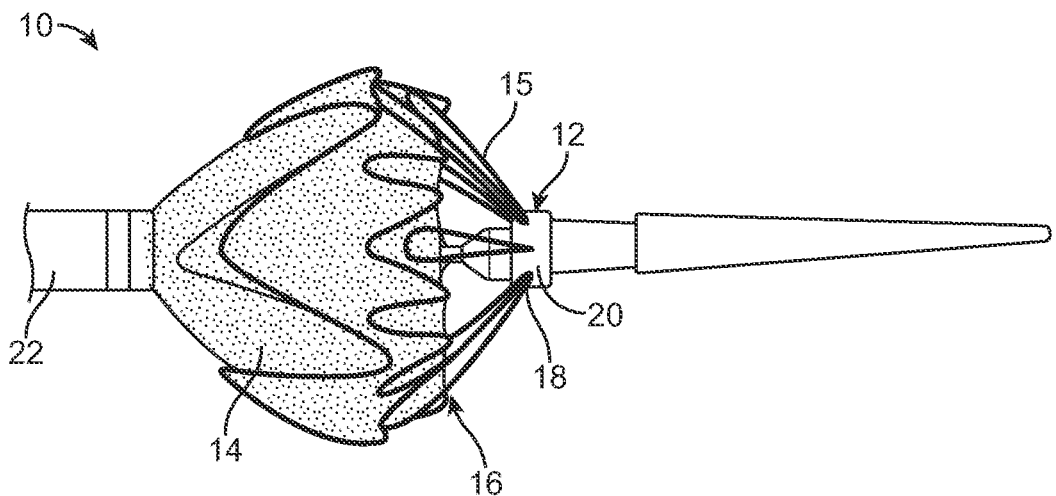
FIGS. 1A and 1B are side views of a distal end of a delivery system having a tip capture mechanism designed to couple or interact with a stent-graft having an open web or free flow proximal end configuration.

Specific embodiments of the present invention are now described with reference to the figures, wherein like reference numbers indicate identical or functionally similar elements. Specific embodiments are now described with reference to the figures, wherein like reference numbers indicate identical or functionally similar elements. Unless otherwise indicated, for the delivery system the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. For the stent graft device proximal is the portion nearer the heart by way of blood flow path while distal is the portion of the stent graft further from the heart by way of blood flow path. In addition, the term "self-expanding" is used in the following description with reference to one or more stent structures of the prostheses hereof and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

The following detailed description is merely exemplary in nature and is not intended to limit the invention or the application and uses of the invention. Although the description of the invention is in the context of treatment of blood vessels such as the coronary, carotid and renal arteries, the invention may also be used in any other body passageways where it is deemed useful. Furthermore, there is no intention to be bound by any expressed or implied theory presented in the preceding technical field, background, brief summary or the following detailed description.

Embodiments hereof relate to a stent-graft having a closed web configuration, and more particularly relate to an apparatus and method for securing endmost crowns or apexes of a self-expanding stent to graft material while still permitting interaction of the endmost crowns with tip capture fingers or prongs of a delivery system. As will be explained in more detail below, the graft covers the endmost crowns of the stent but the endmost crowns are not coupled to the graft material and thus are free to interact with the delivery system. Stoppers are coupled to the stent adjacent to each unattached endmost crown in such a manner as to prevent slippage of the graft material at the endmost crowns and to secure a longitudinal position of the graft material relative to the stent. Additional description and features are described below with reference to the figures.

Referring to FIG. 2, stent-graft prosthesis 200 includes a tubular graft 210 having a first edge or end 202, a second edge or end 204, and a body 203 there between which defines a lumen (not shown) through stent-graft prosthesis 200. In an embodiment, first end 202 of graft 210 may be referred to as a proximal end of graft 210 and a proximal end of stent-graft prosthesis 200, which is conventionally the end that is coupled to a tip capture mechanism of a delivery system, and second end 204 of graft 210 may be referred to as a distal end of graft 204 and a distal end of stent-graft prosthesis 200. Graft 210 may be formed from any suitable graft material, for example and not limited to, a low-porosity woven or knit polyester, DACRON material, expanded polytetrafluoroethylene, polyurethane, silicone, or other suitable materials. In another embodiment, the graft material could also be a natural material such as pericardium or another membranous tissue such as intestinal submucosa.

Figure 1B:
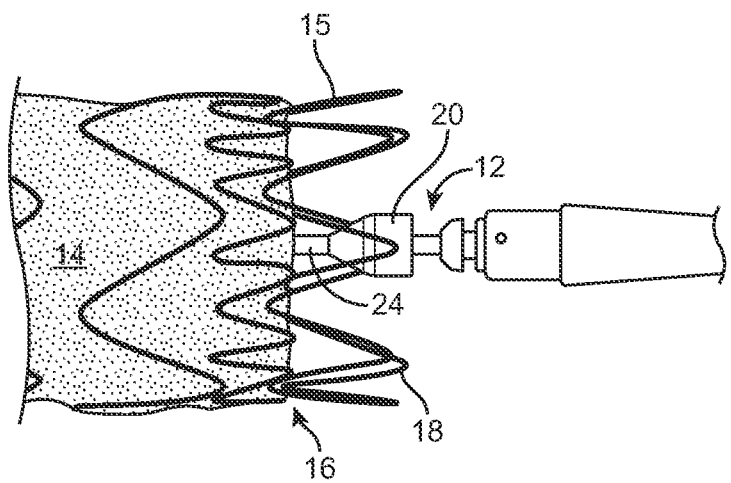

Stent-graft prosthesis 200 also includes at least one radially-compressible stent or scaffold 206 that is coupled to graft 210 for supporting the graft material and is operable to self-expand into apposition with an interior wall of a body vessel (not shown). In the embodiment depicted in FIG. 1, stent-graft prosthesis 200 includes a series of six independent or separate cylindrical stents 206. Each stent 206 is constructed from a self-expanding or spring material, such as Nitinol, and is a sinusoidal patterned ring including a plurality of crowns or bends 208 and a plurality of struts or straight segments 209 with each crown being formed between a pair of opposing struts. Although shown with six stents, it will be understood by those of ordinary skill in the art that stent-graft prosthesis 200 may include a greater or smaller number of sinusoidal patterned rings depending upon the desired length of stent-graft prosthesis 200 and/or the intended application thereof. For description purposes only, the stent that is coupled adjacent and proximate to first end 202 of graft 210 is referred to herein as first end stent 206A and the stent that is coupled adjacent and proximate to second end 204 of graft 210 is referred to herein as second end stent 206B but it will be understood by those of ordinary skill in the art that all of the stents may have identical or different patterns or configurations. Stents 206 are coupled to graft 210 by stitches 212 or other means known to those of skill in the art. In the embodiment shown in FIG. 2, stents 206 are coupled to an inside surface of graft 210. However, stents 206 may alternatively be coupled to an outside surface of graft 210. When stent-graft 200 is used for treating an aneurysm, stents 206 have sufficient radial spring force and flexibility to conformingly engage stent-graft prosthesis 200 with the body lumen inner wall, to avoid excessive leakage, and prevent pressurization of the aneurysm, i.e., to provide a leak-resistant seal. Although some leakage of blood or other body fluid may occur into the aneurysm isolated by stent-graft prosthesis 200, an optimal seal will reduce the chances of aneurysm pressurization and resulting rupture.

In another embodiment (not shown), rather than a series of independent or separate self-expanding stents/sinusoidal patterned rings, the support structure or scaffolding of stent-graft prosthesis 200 may have other configurations such as a series of sinusoidal patterned rings coupled to each other to form a self-expanding stent.

At least first end 202 of stent-graft prosthesis 200 has a closed web configuration in which the endmost crowns 208 of end stent 206A are covered or lined by graft 210 and do not extend past or beyond first end 202 of graft 210. As used herein, "endmost" crowns are the crowns or peaks of a stent that are most proximate to and inwardly spaced apart from an end or edge of graft 210, such as first end or edge 202. In the embodiment of FIG. 2, end stents 206A is coupled to the graft material so as to have a first or endmost set of crowns 208 adjacent to the first end 202 of graft 210 and a second or opposing set of crowns 211 distant from first end 202 of graft 210 relative to the endmost set of crowns. Endmost crowns 208 of first end stent 206A are not coupled or stitched to graft 210 and are free from direct attachment to graft 210, so that the endmost crowns 208 may interact with a tip capture mechanism on a delivery system as previously described herein in relation to FIG. 1A and FIG. 1B. In the embodiment depicted in FIG. 2, the endmost crowns 208B of end stent 206B are also covered or lined by graft 210 and do not extend outside of or beyond the end of graft 210. However, in the embodiment of FIG. 2, the endmost crowns 208B of second end stent 206B are stitched or otherwise secured to graft 210 because such crowns are not used for coupling the prosthesis to the delivery system. In another embodiment (not shown), the endmost crowns 208B of second stent 206B are not coupled or stitched to graft 210 and are free from direct attachment to graft 210 so as to be accessible for attachment to the delivery system. In yet another embodiment (not shown), the endmost crowns 208B of second end stent 206B may extend beyond second end 204 of graft 210 in an open web or free-flow configuration.

A pair of stoppers 214 are coupled to first end stent 206A proximate or adjacent to each unattached endmost crown 208 such that there is a stopper adjacent to opposing sides 230, 232 of the endmost crown as shown in FIG. 2 and FIG. 2A. FIG. 2A illustrates an endmost crown 208 having stoppers 214 but the graft material is not shown for clarity purposes. Each endmost crown 208 is a curved segment formed between a pair of opposing struts 209 as described above, and a first stopper 214 is coupled to the strut adjacent to a first side 230 of each unattached endmost crown 208 and a second stopper 214 is coupled to the opposing or second strut adjacent to an opposing or second side 232 of each unattached endmost crown 208. "Opposing side" of an endmost crown as used herein refers a point or location on the stent wire or wire-like structure that forms the stent where the crown transitions to the strut, i.e., where the curved segment transitions to the straight segment. The location of each stopper on each strut may vary according to application, but each stopper is at least spaced apart from the peak or apex of each endmost crown 208 so that the endmost crowns 208 may be used to couple prosthesis 200 to a delivery system having a tip capture mechanism.

Referring to FIG. 3, in one embodiment hereof, each stopper 214 has a tubular configuration and includes a cylindrical body 320 defining a lumen 324 there through. Cylindrical body 320 includes an outer diameter $D_O$ and an inner diameter $D_I$. Inner diameter $D_I$ is equal to or slightly greater than an outer diameter of stent strut 209 such that stopper 214 may be fitted there over. Outer diameter $D_O$ is greater than inner diameter $D_I$ and accordingly is greater than the outer diameter of stent strut 209.

Cylindrical body 320 includes a slit or slot 322 extending through the wall thereof and extending the entire length thereof, i.e., has a slit-tube configuration, which allows each stopper 214 to be placed or clipped directly onto a stent, for instance first end stent 206A. During assembly or manufacture of stent-graft prosthesis 200, stoppers 214 are first positioned on first end stent 206A such that there is a stopper on opposing struts of each unattached endmost crown 208.

Figure 4:
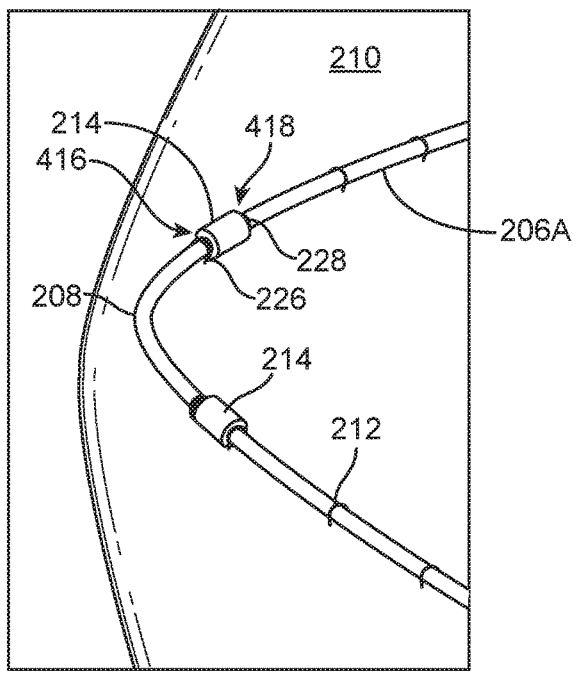
Figure 5:
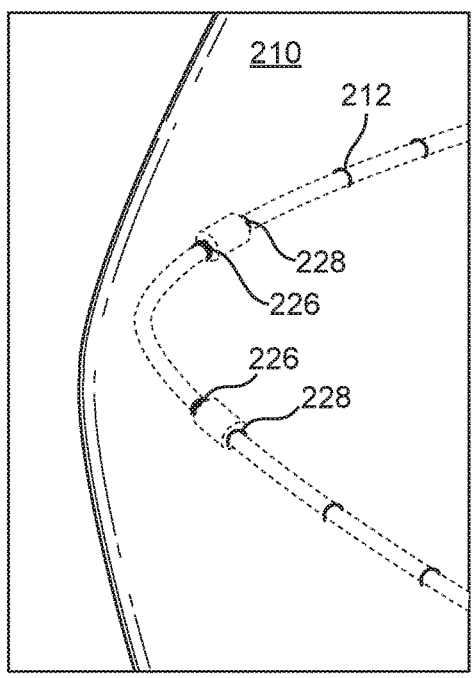

After being properly positioned, each stopper 214 is crimped and bonded onto stent strut 209. Graft 210 is then secured to first end stent 206A adjacent first and second ends 416, 418, respectively, of each stopper 214. Adjacent to second end 418 of stopper 214, graft 210 is secured to first end stent 206A with at least one stitch or suture 228 (see FIG. 2 and FIGS. 4-5). Adjacent to first end 416 of stopper 214, graft 210 is secured to first end stent 206A with at least one stitch 226 (see FIG. 2 and FIGS. 4-5). In an embodiment, stitch 226 is a double stitch 226, which is stronger than a single stitch, and is positioned adjacent to first end 416 of stopper 214 to ensure that graft 210 is secure against each stopper 214. In another embodiment (not shown), stitch 226 may be a triple stitch to secure graft 210 to first end stent 206A adjacent to the first end 416 of each stopper 214.

Stitches 226, 228 secure the longitudinal position of the graft material of graft 210 with respect to stopper 214 and strut 209 to which stopper 214 is attached, and accordingly stopper 214 together with stitches 226, 228 prevent the graft material of graft 210 from undesirable shifting or slipping during operation. More particularly, stitches 226, 228 abut against and contact end faces of first and second ends 416, 418, respectively, of stopper 214 and are not permitted to pass or slip over the stopper since stopper 214 has outer diameter $D_O$ which is greater than the outer diameter of stent strut 209. Since the outer diameter $D_O$ of each stopper is greater than an outer diameter of struts 209, end faces 317, 319 of stopper ends 416, 418, respectively, create a raised feature along or relative to the surface of strut 209 against which stitches 226, 228 may bear during loading and/or deployment procedures concerning stent-graft prosthesis 200, and thereby prevent shifting or slippage of graft material relative to stopper 214. Without a stopper in place and endmost crowns 208 unattached to graft 210, the graft material covering or lining the endmost crowns may slip or move and cause undesired bunching and/or wrinkling of graft 210 during loading and/or deployment procedures. If the graft material slips, bunches, or wrinkles, the graft material may become misaligned and endmost crowns 208 may be undesirably exposed after deployment of stent-graft prosthesis 200. However, stoppers 214 ensure that graft 210 does not slip distally or downwards at endmost crowns 208 but rather remains covering the endmost crowns 208.

In an embodiment, stoppers 214 are made of a radiopaque material such as but are not limited to tungsten, tantalum, platinum, platinum and iridium alloy, rhenium, gold, molybdenum, silver, and alloys containing one or more thereof. When formed of a radiopaque material, stoppers 214 advantageously operate as radiopaque markers to track the position of first end stent 206A within the body. In another embodiment, stoppers 214 may be formed from stainless steel or other suitable material.

FIG. 6 illustrates another configuration of a stopper which operates to prevent a graft from undesirable shifting or slipping away from unattached endmost crowns. Similar to stopper 214, stopper 614 has a tubular configuration and includes a cylindrical body 620 defining a lumen 624 there through. However, cylindrical body 620 does not include a slit or slot extending through the wall thereof. During manufacture, prior to formation of end stent 206A into a ring, a stopper 614 is positioned on the wire that is to form end stent 206A such that there is a stopper on opposing struts of each crown that is to form an unattached endmost crown of the finished stent. After being properly positioned, each stopper 614 is crimped and bonded onto the stent wire and the stent wire is formed into a ring, i.e., the ends of the sinusoidal wire are crimped together. Graft material may then be secured to the end stent as described above with respect to stopper 214.

FIG. 7 illustrates a stent-graft prosthesis 700 according to another embodiment hereof in which the prosthesis includes a tubular radially-compressible stent or scaffold 706 rather than a plurality of stents formed as independent sinusoidal patterned rings. Stent 706 is coupled within a tubular graft 710 to extend from a first end 702 to a second end 704 thereof for supporting the graft material and is operable to self-expand into apposition with an interior wall of a body vessel (not shown). In the embodiment depicted in FIG. 7, stent 706 is a unitary tubular component having diamond-shaped openings 734, which may be formed by various conventional stent forming methods as would be understood by one of ordinary skill in the art. Stent 706 includes endmost crowns 708 that are proximate to and inwardly spaced from an edge or end 702 of graft 710. Each endmost crown 708 is a curved segment extending between opposing struts 709 on stent 706. Stoppers 714, which are similar to stoppers 214 described above, are coupled onto each strut 709 adjacent to opposing sides 730, 732 of each endmost. The location of each stopper on each strut may vary according to application, but as described above with respect to stoppers 714, the distance between the peak or apex of each endmost crown 708 and stopper 714 is sufficient to utilize the endmost crowns to couple prosthesis 700 to a delivery system having a tip capture mechanism. Similar to stopper 214, at least one stitch is made adjacent to each end of each stopper 714 in order to couple graft material of graft 710 to stent 706, although such stitches are not shown in FIG. 7 for sake of clarity.

While various embodiments according to the present invention have been described above, it should be understood that they have been presented by way of illustration and example only, and not limitation. For example, although the stoppers are illustrated on the first or proximal end of the tubular graft which is conventionally coupled to a tip capture mechanism of a delivery system, it would be understood by one of ordinary skill in the art that the stoppers and respective stitches may also or alternatively be coupled adjacent to endmost crowns of a stent proximate the second or distal end of the tubular graft depending on the delivery system used to deliver the stent-graft. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:
1. A prosthesis for implantation within a body lumen, the prosthesis comprising:
   a tubular graft of a graft material;
   a stent comprised of a plurality of crowns and a plurality of struts with each crown being formed between a pair of opposing struts, the stent being coupled to the graft material proximate to an end of the tubular graft so as to have a first set of crowns adjacent to the end of the tubular graft and a second set of crowns distant from the end of the tubular graft relative to the first set of crowns;
a pair of stoppers coupled adjacent to each crown of the first set of crowns, wherein each stopper has a tubular configuration and is attached to a respective one of the pair of opposing struts that the crown is formed between; and
at least one stitch made adjacent to each end of each stopper, wherein the stitches abut against and contact an end face of each stopper in order to secure a longitudinal position of the graft material relative to each stopper and the strut it is attached to such that the first set of crowns are covered by and free of direct attachment to the graft material of the tubular graft.

2. The prosthesis of claim 1, wherein each stopper is a cylindrical body defining a lumen there through.

3. The prosthesis of claim 2, wherein the cylindrical body includes a slit through a wall of the cylindrical body that extends the entire length of the cylindrical body.

4. The prosthesis of claim 1, wherein the graft material is secured to the stent with a single stitch adjacent to a first end of each stopper and wherein the graft material is secured to the stent with at least a double stitch adjacent to a second end of each stopper, the second end of each stopper being closer to the crown than the first end of each stopper.

5. The prosthesis of claim 1, wherein each stopper is formed of a radiopaque material.

6. The prosthesis of claim 1, further comprising: a plurality of stents coupled to a body of the tubular graft, wherein each stent is a sinusoidal patterned ring formed from a self-expanding material.

7. The prosthesis of claim 1, wherein the stent is coupled to an inside surface of the tubular graft.

8. A prosthesis for implantation within a body lumen, the prosthesis comprising:
a tubular graft of a graft material;
a stent coupled to the tubular graft and having endmost crowns that are inwardly spaced from a first end of the tubular graft, each endmost crown being a curved segment formed between a pair of opposing struts, wherein one or more of the endmost crowns are covered by and free of direct attachment to the graft material of the tubular graft;
a pair of stoppers coupled adjacent to each endmost crown that is covered by and free of direct attachment to the graft material, wherein each stopper has a tubular configuration and is attached to a respective one of the pair of opposing struts that the crown is formed between; and
at least one stitch made adjacent to each end of each stopper, wherein the stitches abut against and contact an end face of each stopper in order to secure a longitudinal position of the graft material relative to each stopper and the strut it is attached to.

9. The prosthesis of claim 8, wherein each stopper is a cylindrical body defining a lumen there through.

10. The prosthesis of claim 9, wherein the cylindrical body includes a slit through a wall of the cylindrical body that extends the entire length of the cylindrical body.

11. The prosthesis of claim 8, wherein the graft material is secured to the stent with a single stitch adjacent to a first end of each stopper and wherein the graft material is secured to the stent with at least a double stitch adjacent to a second end of each stopper, the second end of each stopper being closer to the endmost crown than the first end of each stopper.

12. The prosthesis of claim 8, wherein each stopper is formed of a radiopaque material.

13. The prosthesis of claim 8, wherein the stent is coupled to the tubular graft to extend from the first end of the tubular graft to a second end of the tubular graft.

14. The prosthesis of claim 8, further comprising: a plurality of stents coupled to a body of the tubular graft, wherein each stent is a sinusoidal patterned ring formed from a self-expanding material.

15. A prosthesis for implantation within a body lumen, the prosthesis comprising:
a tubular graft of a graft material;
a stent coupled to the tubular graft and including a plurality of crowns and a plurality of struts with each crown being formed between a pair of opposing struts, the stent having endmost crowns that are proximate to an end of the tubular graft, wherein one or more of the endmost crowns are covered by and free of direct attachment to the graft material of the tubular graft;
a pair of stoppers coupled adjacent to each endmost crown that is covered by and unattached to the graft material, wherein each stopper is attached to a respective one of the pair of opposing struts that the crown is formed between to be longitudinally fixed in position relative thereto and an outer diameter of each stopper is greater than an outer diameter of the struts such that each stopper end is a raised feature relative to the respective strut; and
at least one stitch made adjacent to each end of each stopper, wherein the stitches abut against and contact the respective raised feature of each stopper end in order to secure a longitudinal position of the graft material relative to each stopper and the strut it is attached to.

16. The prosthesis of claim 15, wherein each stopper is a cylindrical body defining a lumen there through and the raised feature is an end surface thereof.

17. The prosthesis of claim 16, wherein the cylindrical body includes a slit through a wall of the cylindrical body that extends the entire length of the cylindrical body.

18. The prosthesis of claim 15, wherein the graft material is secured to the stent with a single stitch adjacent to a first end of each stopper and wherein the graft material is secured to the stent with at least a double stitch adjacent to a second end of each stopper, the second end of each stopper being closer to the crown than the first end of each stopper.

19. The prosthesis of claim 15, wherein each stopper is formed of a radiopaque material.

20. The prosthesis of claim 15, further comprising: a plurality of stents coupled to a body of the tubular graft, wherein each stent is a sinusoidal patterned ring formed from a self-expanding material.

* * * * *